(12) United States Patent
Lin

(10) Patent No.: US 11,476,004 B2
(45) Date of Patent: Oct. 18, 2022

(54) SYSTEM CAPABLE OF ESTABLISHING MODEL FOR CARDIAC VENTRICULAR HYPERTROPHY SCREENING

(71) Applicant: HUALIEN ARMED FORCES GENERAL HOSPITAL, Xincheng Township, Hualien County (TW)

(72) Inventor: Gen-Min Lin, Taipei (TW)

(73) Assignee: HUALIEN ARMED FORCES GENERAL HOSPITAL, Xincheng Township, Hualien County (TW)

( * ) Notice: Subject to any disclaimer, the term of this patent is extended or adjusted under 35 U.S.C. 154(b) by 629 days.

(21) Appl. No.: 16/599,893

(22) Filed: Oct. 11, 2019

(65) Prior Publication Data

US 2021/0110933 A1   Apr. 15, 2021

(51) Int. Cl.
| | |
|---|---|
| G06V 20/00 | (2022.01) |
| G16H 50/50 | (2018.01) |
| G06N 20/10 | (2019.01) |
| G06K 9/00 | (2022.01) |
| A61B 5/319 | (2021.01) |
| A61B 5/366 | (2021.01) |

(52) U.S. Cl.
CPC ........... *G16H 50/50* (2018.01); *A61B 5/319* (2021.01); *A61B 5/366* (2021.01); *G06K 9/00536* (2013.01); *G06N 20/10* (2019.01)

(58) Field of Classification Search
CPC ......... G06N 3/02; G06N 3/4046; G06N 3/08; G06N 20/10; G06N 20/00; A61B 5/04021; A61B 5/0472; G06K 9/00536; G06V 30/191; G16H 50/50; G06T 2207/20081
See application file for complete search history.

(56) References Cited

U.S. PATENT DOCUMENTS

| | | | | |
|---|---|---|---|---|
| 5,862,304 A * | 1/1999 | Ravdin | ............... | G16H 50/20 706/924 |
| 6,658,396 B1* | 12/2003 | Tang | ............... | G16H 20/10 706/17 |
| 9,595,120 B2* | 3/2017 | Nguyen | ............... | G06T 7/0012 |
| 9,700,219 B2* | 7/2017 | Sharma | ............... | G16H 50/20 |
| 10,140,421 B1* | 11/2018 | Bernard | ............... | A61B 8/468 |
| 10,140,544 B1* | 11/2018 | Zhao | ............... | G06V 10/454 |
| 10,347,010 B2* | 7/2019 | Risman | ............... | G06N 3/08 |
| 10,499,857 B1* | 12/2019 | Nguyen | ............... | G06V 10/82 |
| 11,334,791 B2* | 5/2022 | Singh | ............... | G06N 3/08 |
| 11,354,791 B2* | 6/2022 | Tsymbalenko | ............... | G06T 5/50 |
| 11,373,304 B2* | 6/2022 | Katscher | ............... | G06T 7/0012 |
| 2014/0065648 A1* | 3/2014 | Wienhues-Thelen | ............... | G01N 33/6887 422/69 |

* cited by examiner

*Primary Examiner* — Amir Alavi
(74) *Attorney, Agent, or Firm* — Fox Rothschild LLP; Robert J. Sacco (57) ABSTRACT

A system for establishing a model for cardiac ventricular hypertrophy (VH) screening includes a storage and a processor. The storage stores multiple pieces of subject data respectively associated with multiple subjects. Each of the pieces of subject data contains a basic physiological parameter group, an electrocardiographic parameter group, and an actual VH condition that corresponds to a left or right ventricle of the subject associated with the piece of subject data. The processor is electrically connected to the storage, splits the pieces of subject data into a training set and a test set, and establishes the model for VH screening based on the pieces of subject data in the training set by using machine learning techniques.

11 Claims, 7 Drawing Sheets

SYSTEM CAPABLE OF ESTABLISHING MODEL FOR CARDIAC VENTRICULAR HYPERTROPHY SCREENING

FIELD

The disclosure relates to a system capable of establishing a model, and more particularly to a system capable of establishing a model for cardiac ventricular hypertrophy (VH) screening.

BACKGROUND

Conventionally, left ventricular hypertrophy (VH) is diagnosed through 12-lead electrocardiogram in population health examinations most commonly by using the Cornell or the Sokolow-Lyon voltage criteria. A male is diagnosed with left VH when a condition "aVL-R+V3-S≥28 mm" is satisfied under the Cornell voltage criterion, or when a condition "max[(V1-S or V2-S)+(V5-R or V6-R)] 35 mm" is satisfied when the Sokolow-Lyon voltage criterion is used, where 1 mm in amplitude of an electrocardiogram corresponds to 0.1 mV in magnitude of the heart's electrical potential recorded by the electrocardiogram.

Similarly, right VH is diagnosed through 12-lead electrocardiogram frequently by using the Sokolow-Lyon voltage criterion or the voltage criteria established by Myers et al. A male is diagnosed with right VH when a condition "max [V1-R+(V5-S or V6-S)] >10.5 mm" is satisfied according to the Sokolow-Lyon voltage criterion, or when any one of the following conditions is satisfied under the voltage criteria established by Myers et al.: "V1-R/V1-S>1", "V5-R/V5-S<1", "V6-R/V6-S<1 " or "V1-R>6 mm".

Data extracted from 12-lead electrocardiogram (e.g., voltage amplitude, wave duration or electrical axis) have been utilized in machine learning to screen for left VH but not yet to screen for right VH. Moreover, the sensitivity of the aforesaid conventional electrocardiogram-based approaches of left or right VH screening is usually lower than 30%, and it is unreliable to screen for cardiac VH using the aforementioned approaches that are solely based on data extracted from the 12-lead electrocardiogram.

SUMMARY

Therefore, the objective of the disclosure is to provide a system capable of establishing a model for cardiac ventricular hypertrophy (VH) screening that can alleviate at least one of the drawbacks of the prior art by using physiological parameters and electrocardiographic parameters.

According to the disclosure, the system includes a storage and a processor. The storage is configured to store plural pieces of subject data that are respectively associated with a plurality of subjects. Each of the pieces of subject data contains a basic physiological parameter group, an electrocardiographic parameter group, and an actual cardiac VH condition that corresponds to a specified ventricle of one of the subjects associated with the piece of subject data. The specified ventricle is one of a left ventricle and a right ventricle. The processor is electrically connected to the storage, and is configured to split the pieces of subject data into a training set and a test set, and to establish the model for cardiac VH screening with respect to the specified ventricle based on the pieces of subject data in the training set by using machine learning techniques.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

Figure 1:
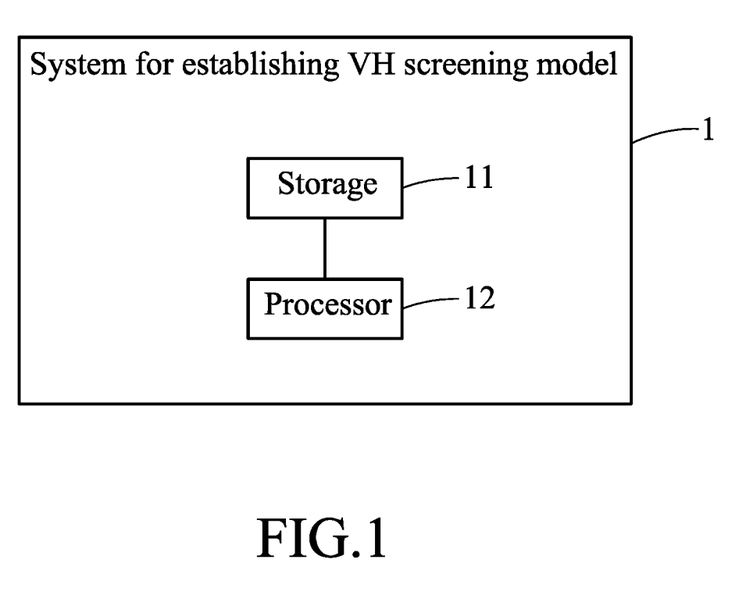
FIG. 1 is a block diagram illustrating an embodiment of a system capable of establishing a model for cardiac ventricular hypertrophy (VH) screening according to the disclosure.

Referring to FIG. 1, an embodiment of a system 1 capable of establishing a model for cardiac ventricular hypertrophy (VH) screening (also referred to as VH screening model) is illustrated. The system 1 includes a storage 11 and a processor 12. The processor 12 is electrically connected to the storage 11.

The storage 11 is configured to store plural pieces of subject data that are respectively associated with a plurality of subjects. Each of the pieces of subject data contains a basic physiological parameter group, an electrocardiographic parameter group, and an actual cardiac VH condition that corresponds to a specified ventricle of one of the subjects associated with the piece of subject data and that represents an actual result of previously-made determination on whether or not the subject has cardiac VH (e.g., determined by a medical professional using ultrasonography). The specified ventricle is one of a left ventricle and a right ventricle. In this embodiment, the subjects are young adults, but are not limited thereto. It should be noted that for each of the pieces of subject data to be used in machine learning, a combination of the basic physiological parameter group and the electrocardiographic parameter group serves as input feature data, and the actual cardiac VH condition serves as a label corresponding to the input feature data.

The basic physiological parameter group contains values respectively related to an age, a body height and a body weight of the associated one of the subjects.

The electrocardiographic parameter group contains values respectively related to a heart rate, a P wave duration in lead II (II-P), a duration of PR segment in lead II (II-PR), a duration of QRS complex in lead II (II-QRS), a duration of QT interval in lead II (II-QT), a duration of corrected QT interval in lead II (II-QTc), a P wave axis in lead II (II-P axis), a QRS axis in lead II (II-QRS axis), a T wave axis in lead II (II-T axis), an amplitude of R wave in lead I (I-R), an amplitude of R wave in lead II (II-R), an amplitude of R wave in lead III (III-R), an amplitude of R wave in lead augmented vector right (aVR-R), an amplitude of R wave in lead augmented vector left (aVL-R), an amplitude of S wave in lead augmented vector left (aVL-S), an amplitude of R wave in lead augmented vector foot (aVF-R), an amplitude of R wave in precordial lead V1 (V1-R), an amplitude of S wave in precordial lead V1 (V1-S), an amplitude of R wave in precordial lead V2 (V2-R), an amplitude of S wave in precordial lead V2 (V2-S), an amplitude of R wave in precordial lead V3 (V3-R), an amplitude of S wave in precordial lead V3 (V3-S), an amplitude of R wave in precordial lead V4 (V4-R), an amplitude of S wave in precordial lead V4 (V4-S), an amplitude of R wave in precordial lead V5 (V5-R), an amplitude of S wave in precordial lead V5 (V5-S), an amplitude of R wave in precordial lead V6 (V6-R) and an amplitude of S wave in precordial lead V6 (V6-S) recorded in an electrocardiogram of the associated one of the subjects. The heart rate is recorded in beats per minute (bpm).

It is worth to note that the specified ventricle is the same for all the pieces of subject data; namely, all of the actual cardiac VH conditions of the pieces of subject data relate to the same VH type (i.e., either all relating to the left VH or all relating to the right VH). In this embodiment, the actual left VH condition (i.e., whether a subject is diagnosed with left VH) is pre-determined based on values of left ventricular mass (LVM), and on one of body surface area (BSA) and body height (Ht) of the subject, where the value of LVM is calculated based on values of left ventricular internal diameter in diastole (LVIDd), posterior wall thickness in diastole (PWTd), and inter ventricular septal thickness at end diastole (IVSTd) that are observed from a result of ultrasonography. For example, a young adult male would be diagnosed with left VH when it is determined that $LVM/BSA \geq 116$ g/m$^2$ or $LVM/Ht^{2.7} \geq 49$ g/m$^{2.7}$. In this embodiment, the actual right VH condition (i.e., whether a subject is diagnosed with right VH) is pre-determined based on the value of right ventricular anterior wall thickness (RVWT) that is observed from a result of ultrasonography. For example, a young adult male would be diagnosed with right VH when it is determined that RVWT>5.5 mm.

The processor 12 is configured to split the pieces of subject data into two sets, namely a training set and a test set, and to establish the model for cardiac VH screening with respect to the specified ventricle based on the pieces of subject data in the training set by using machine learning techniques.

Figure 2:
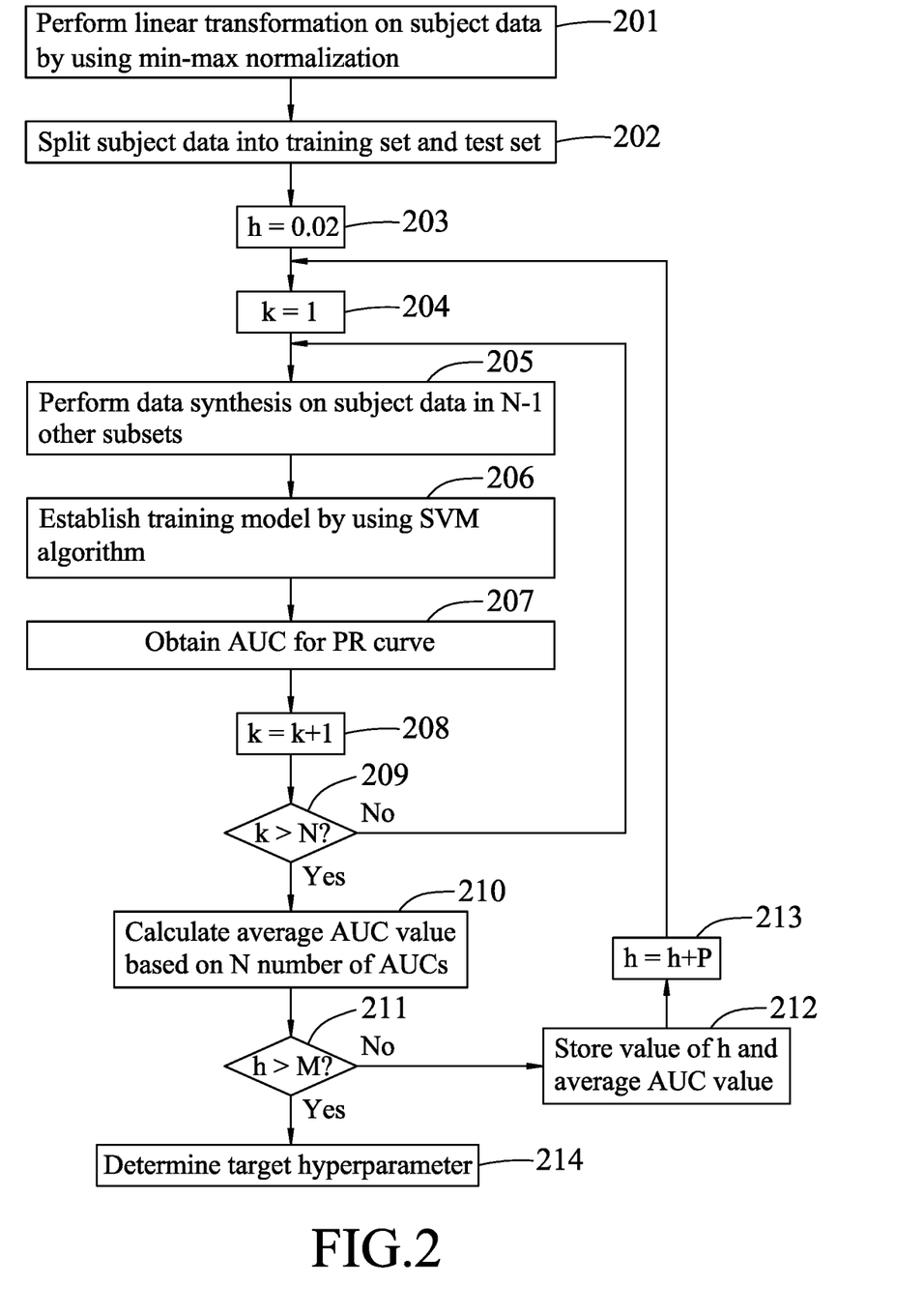
FIG. 2 is a flow chart illustrating an embodiment of a target-hyperparameter-determining procedure performed by the system according to the disclosure.
Figure 4:
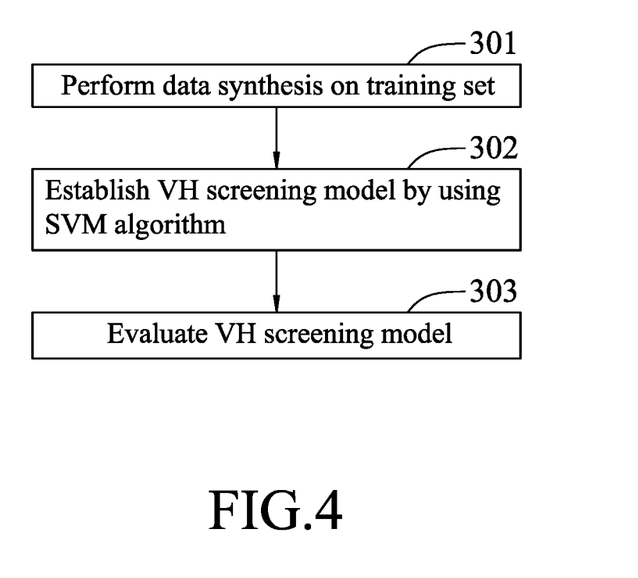
FIG. 4 is a flow chart illustrating an embodiment of a model establishment process performed by the system according to the disclosure.

Referring to FIGS. 1, 2 and 4, an embodiment of a method for establishing the VH screening model according to the disclosure is illustrated. The method is to be implemented by the processor 12 of the system 1. In performing the method according to the disclosure, the processor 12 is configured to establish, by using a support vector machine (SVM) algorithm, the VH screening model based on a target hyperparameter used in the SVM algorithm and the pieces of subject data in the training set. The method includes a target-hyperparameter determination process and a model establishment process.

Referring to FIGS. 1 and 2, the target-hyperparameter determination process of the method includes steps 201 to 214 outlined below.

In step 201, in order to enhance convergence speed of algorithm and effect of training, the processor 12 performs linear transformation on the pieces of subject data by using min-max normalization so as to generate plural pieces of normalized subject data, where the values contained in the basic physiological parameter group and the electrocardiographic parameter group are each mapped into a numeric range [0,1] in the normalized subject data.

In step 202, the processor 12 splits the pieces of normalized subject data into the training set and the test set. The training set includes N number of training subsets (hereinafter referred to as "N training subsets" in short), where N is an integer greater than one. In this embodiment, the ratio of the number of the pieces of normalized subject data in the training set to that in the test set is 4 to 1, but is not limited thereto.

An outline of steps 203 to 214 is provided as follows. The processor 12 is configured to, for each of candidate hyperparameters that are used in the SVM algorithm, perform an area under curve (AUC) calculation procedure N number of times so as to obtain N number of AUCs of precision-recall (PR) curves corresponding to the candidate hyperparameter, where the N number of times of performing the AUC calculation procedure respectively correspond to the N training subsets.

Subsequently, the processor 12 is configured to, for each of the candidate hyperparameters, calculate an average AUC value based on the N number of AUCs obtained through the N number of times of performing the AUC calculation procedure for the candidate hyperparameter. Thereafter, the processor 12 is further configured to determine, based on the average AUC values calculated respectively for the candidate hyperparameters, one of the candidate hyperparameters to serve as the target hyperparameter. It should be noted that in one embodiment, the candidate hyperparameters may be hyperparameters used for another type of machine learning algorithms different from the SVM algorithm mentioned herein. In one embodiment, each of the candidate hyperparameters may be a regularization parameter.

Specifically speaking, the processor 12 is configured to execute the following actions in each performance of the AUC calculation procedure for each of the candidate hyperparameters. First, for the performance of the AUC calculation procedure, the processor 12 selects the corresponding one of the N training subsets as a validation subset, and obtains N-1 other subsets which are all the N training subsets except the validation subset. Subsequently, the processor 12 performs data synthesis on the pieces of normalized subject data in the N-1 other subsets to generate plural pieces of synthetic subject data, and establishes, by using the SVM algorithm based on the pieces of normalized subject data in the N-1 other subsets and the candidate hyperparameter, a training model corresponding to the candidate hyperparameter. Thereafter, the processor 12 obtains, based on the training model and the pieces of normalized subject data in the validation subset, the PR curve corresponding to the candidate hyperparameter, and calculates the AUC for said PR curve. Details of steps 203 to 214 are described as follows.

In step 203, the processor 12 sets an initial value of a hyperparameter variable (h) as 0.02, (i.e., h=0.02) to serve as one of the candidate hyperparameters to be used in the SVM algorithm, but the initial value of the hyperparameter variable (h) is not limited to the disclosure herein and may vary in other embodiments.

In step 204, the processor 12 sets an initial value of a loop counter (k) as one (i.e., k=1). It is worth to note that the value of the loop counter corresponds to the number of times of performance of the AUC calculation procedure for the candidate hyperparameter (i.e., steps 205 to 207).

In step 205, the processor 12 selects the $k^{th}$ one of the N training subsets, and performs data synthesis on the pieces of normalized subject data in the N-1 other subsets (all training subsets other than the $k^{th}$ one) by using synthetic minority over-sampling technique (SMOTE) so as to generate synthetic minority class samples. It is noted that since subjects diagnosed with cardiac VH would be a minority in a pool of random subjects, those pieces of normalized subject data in the N-1 other subsets indicating that the subjects are diagnosed with cardiac VH are the minority, and those pieces of normalized subject data in the N-1 other subsets indicating that the subjects are determined as not having cardiac VH are the majority. Therefore, the pieces of subject data indicating that the subjects are diagnosed with cardiac VH are said to belong to a minority class, and the pieces of subject data indicating that the subjects are determined as not having cardiac VH are said to belong to a majority class. The synthetic minority class samples generated in step 205 and the pieces of normalized subject data in the N-1 other subsets cooperatively serve as the pieces of synthetic subject data, where the pieces of synthetic subject data belonging to the minority class (i.e., the pieces of synthetic subject data indicating that the subjects are diagnosed with cardiac VH) and the pieces of synthetic subject data belonging to the majority class (i.e., the pieces of synthetic subject data indicating that the subjects are determined as not having cardiac VH) are substantially equal in number, as a result of exploiting SMOTE. In this way, issues of imbalance in the number of the pieces of normalized subject data between the minority class and the majority class is alleviated.

In step 206, the processor 12 establishes the training model corresponding to the candidate hyperparameter which is set in step 203 by using the SVM algorithm based on the candidate hyperparameter and the pieces of synthetic subject data. It should be noted that the algorithm used to establish the training model is not limited to the disclosure herein and may vary in other embodiments. In some embodiments, the processor 12 may establish the training model by using a machine learning algorithm different from the SVM algorithm.

In step 207, the processor 12 obtains the PR curve corresponding to the candidate hyperparameter used for the SVM algorithm in step 206 based on the training model and the pieces of normalized subject data in the validation subset, and calculates the AUC for the PR curve.

Figure 3:
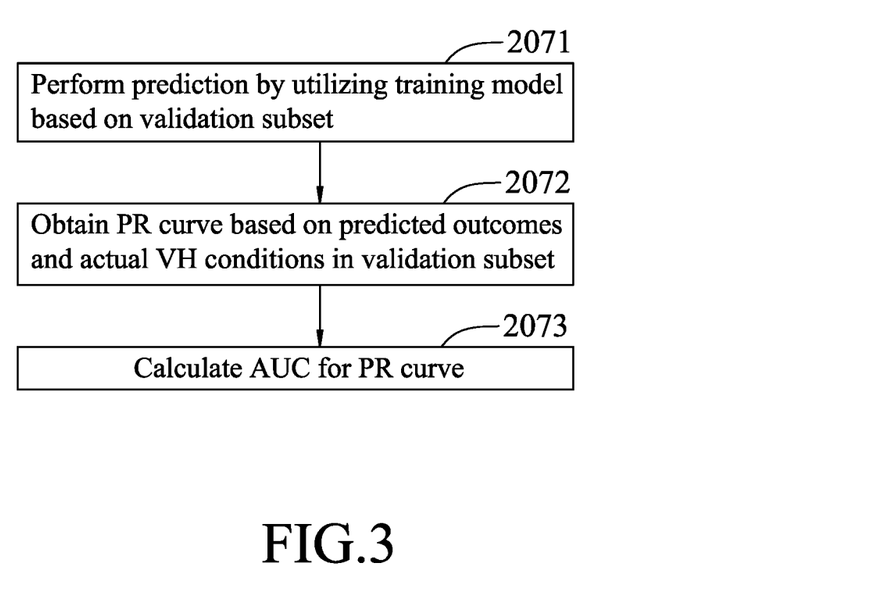
FIG. 3 is a flow chart illustrating an embodiment of an AUC calculation procedure for calculating an area under curve (AUC) for a precision-recall (PR) curve.

Referring to FIG. 3, step 207 includes sub-steps 2071 to 2073. In sub-step 2071, the processor 12 performs prediction on the basic physiological parameter group and the electrocardiographic parameter group contained in each of the pieces of normalized subject data in the validation subset by utilizing the training model, so as to obtain predicted outcomes respectively corresponding to the pieces of normalized subject data in the validation subset.

In sub-step 2072, the processor 12 obtains the PR curve based on the predicted outcomes and the actual cardiac VH conditions contained in the pieces of normalized subject data in the validation subset.

In sub-step 2073, the processor 12 calculates the AUC for the PR curve.

Referring back to FIG. 2, in step 208, the processor 12 increases the value of the loop counter (k) by one (i.e., k=k+1).

In step 209, the processor 12 determines whether the value of the loop counter (k) is greater than N. When it is determined that the value of the loop counter (k) is greater than N, a flow of procedure of the method proceeds to step 210. Otherwise, when it is determined that the value of the loop counter (k) is not greater than N, the flow of procedure goes back to step 205.

In step 210, the processor 12 calculates the average AUC value based on the N number of AUCs obtained through the N times of repetition of the AUC calculation procedure, where the average AUC value corresponds to the one of candidate hyperparameters in step 203.

It is worth to note that in one embodiment, the target-hyperparameter determination process does not include steps 204, 208, 209 and 210. In other words, the target-hyperparameter determination process may skip cross validation. In this scenario, the processor 12 is configured to select an arbitrary one of the N training subsets as the validation subset in step 205, and to calculate only one AUC for the PR curve corresponding to the one of candidate hyperparameters in step 203.

In step 211, the processor 12 determines whether the value of the hyperparameter variable (h) is greater than a threshold value (M). When it is determined that the value of the hyperparameter variable (h) is not greater than the threshold value (M), the flow of procedure proceeds to step 212. Oppositely, when it is determined that the value of the hyperparameter variable (h) is greater than the threshold value (M), the flow of procedure proceeds to step 214. In this embodiment, the threshold value (M) is 1, but is not limited thereto. The threshold value (M) may vary for different machine learning algorithms.

In step 212, the processor 12 stores the value of the hyperparameter variable (h) and the average AUC value in the storage 11. It should be noted that the value of the hyperparameter variable (h) and the average AUC value stored in this step form a corresponding pair. In other words, the stored value of the hyperparameter variable (h) represents the corresponding one of the candidate hyperparameters used in the SVM algorithm to calculate the average AUC.

In step 213, the processor 12 increases the value of the hyperparameter variable (h) by a predetermined constant value (P) (i.e., h=h+P). Then, the flow of procedure goes back to step 204. In this embodiment, the predetermined constant value (P) is 0.001, but is not limited thereto. The predetermined constant value (P) may also vary for different machine learning algorithms.

In step 214, the processor 12 determines one of the candidate hyperparameters based on the values of the hyperparameter variable (h) and the average AUC values that are stored in the storage 11 and makes said one of the candidate hyperparameters serve as the target hyperparameter. In this embodiment, the target hyperparameter is one of the candidate hyperparameters that corresponds to the largest average AUC value among all of the average AUC values, but is not limited thereto. Referring to FIGS. 1 and 4, the model establishment process of the method includes steps 301 to 303 described below.

In step 301, the processor 12 performs data synthesis on the pieces of normalized subject data in the training set to generate plural pieces of synthesized subject data. It should be noted that in this embodiment, the processor 12 is configured to perform data synthesis on the pieces of normalized subject data in the training set by using SMOTE so as to generate synthetic minority class samples, which, together with the pieces of normalized subject data serve as the pieces of synthesized subject data, where the pieces of synthesized subject data belonging to a minority class (i.e., the pieces of synthesized subject data indicating that the subjects are diagnosed with cardiac VH) and the pieces of synthesized subject data belonging to a majority class (i.e., the pieces of synthesized subject data indicating that the subjects are determined as not having cardiac VH) are substantially equal in number.

In step 302, the processor 12 establishes the VH screening model based on the target hyperparameter and the pieces of synthesized subject data by using the SVM algorithm. However, an algorithm used to establish the VH screening model is not limited to the disclosure herein and may vary in other embodiments. In some embodiments, the processor 12 may establish the VH screening model by using a machine learning algorithm different from the SVM algorithm.

In step 303, the processor 12 evaluates the VH screening model based on the pieces of normalized subject data in the test set and a predetermined cut-off point, which is a criterion for determining whether or not a subject has cardiac VH. In this embodiment, the predetermined cut-off point is determined according to a specificity ranging between 70% and 75% when the VH screening model is applied to the pieces of normalized subject data in the test set. However, how to determine the predetermined cut-off point is not limited to the disclosure herein and may vary in other embodiments.

Figure 5:
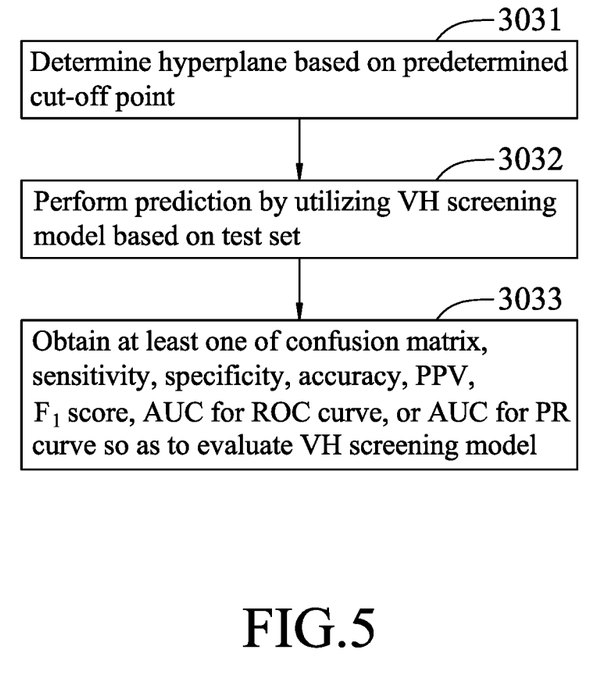
FIG. 5 is a flow chart illustrating an embodiment of model evaluation performed by the system according to the disclosure.

Referring to FIG. 5, step 303 includes sub-steps 3031 to 3033.

In sub-step 3031, the processor 12 determines a hyperplane used in the SVM algorithm based on the predetermined cut-off point.

In sub-step 3032, the processor 12 performs prediction by utilizing the VH screening model based on the basic physiological parameter groups and the electrocardiographic parameter groups contained in all the pieces of normalized subject data in the test set, so as to obtain predicted outcomes respectively corresponding to the pieces of normalized subject data in the test set.

In sub-step 3033, based on the predicted outcomes and the actual cardiac VH conditions contained in the pieces of normalized subject data in the test set, the processor 12 obtains a confusion matrix, a value of sensitivity (also known as "recall"), a value of specificity, a value of accuracy, a positive predictive value (PPV, also known as "precision"), an $F_1$ score, an AUC for a receiver operating characteristic (ROC) curve, an AUC for a PR curve, or any combination thereof in order to evaluate performance of the VH screening model.

For example, in a scenario where the cut-off point is 0.45 and the specified ventricle is the left ventricle, a predicted outcome indicating that a subject may have left VH is obtained when it is determined that a probability is not smaller than 0.45, where the probability results from performing prediction by applying the VH screening model on the basic physiological parameter group and the electrocardiographic parameter group of the piece of normalized subject data corresponding to the subject. Oppositely, a predicted outcome indicating that a subject may not have left VH is obtained when it is determined through the VH screening model that the probability is smaller than 0.45.

In a scenario where the test set contains 2196 pieces of subject data in total, based on 2196 predicted outcomes respectively corresponding to the 2196 pieces of subject data, the processor 12 obtained a confusion matrix as shown in Table 1 below. Specifically speaking, the 2196 predicted outcomes can be divided into two groups, one containing 2046 predicted outcomes that correspond to subjects who do not have left VH (actual negatives), and the other containing 150 predicted outcomes that correspond to subjects who have left VH (actual positives). For the confusion matrix, 1531 out of the 2046 predicted outcomes each indicating that the corresponding subject is predicted as not having left VH are true negatives (TNs) because the 1531 predicted outcomes are correct (meaning that the predictions of not having left VH are true, i.e., matching the actual left VH conditions), and 515 out of the 2046 predicted outcomes each indicating that the corresponding subject is predicted as having left VH are false positives (FPs) because the 515 predicted outcomes are incorrect (meaning that the predictions of having left VH are false, i.e., contrary to the actual left VH conditions). Similarly, 121 out of the 150 predicted outcomes each indicating that the corresponding subject is predicted as having left VH are true positives (TPs) because the 121 predicted outcomes are correct (meaning that the predictions of having left VH are true), and 29 out of the 150 predicted outcomes each indicating that the corresponding subject is predicted as not having left VH are false negatives (FNs) because the 29 predicted outcomes are incorrect (meaning that the predictions of not having left VH are false).

TABLE 1

|  | Predicted: Without left VH | Predicted: With left VH |
|---|---|---|
| Actual: Without left VH | 1531 | 515 |
| Actual: With left VH | 29 | 121 |

Figure 6:
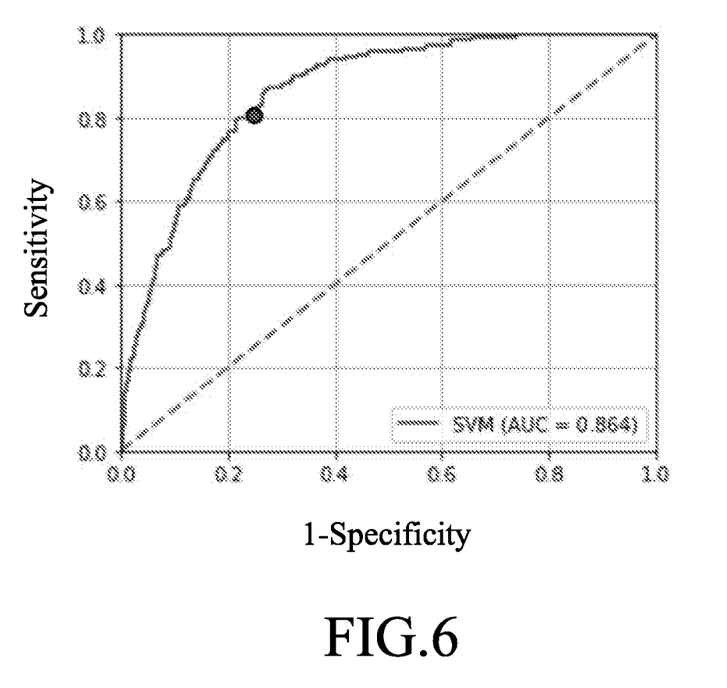
FIG. 6 is a schematic diagram illustrating an embodiment of a receiver operating characteristic (ROC) curve.
Figure 7:
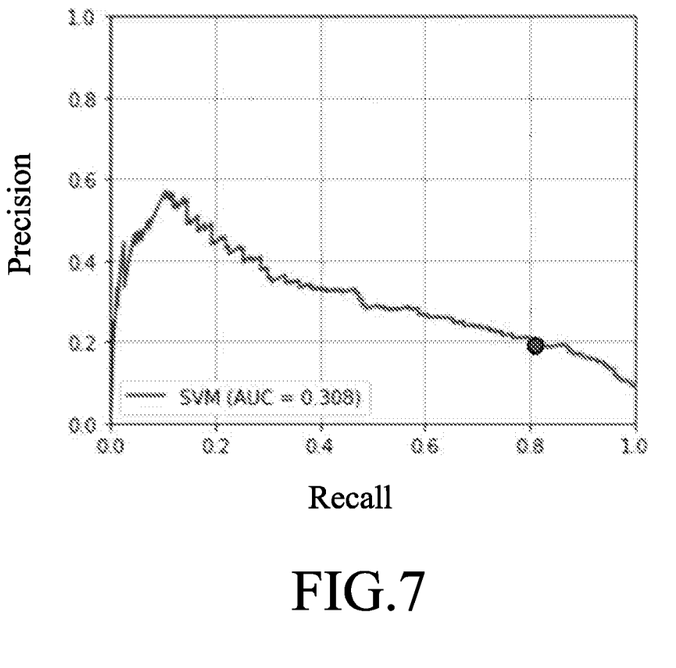
FIG. 7 is a schematic diagram illustrating an embodiment of the PR curve.

Based on the confusion matrix as shown in Table 1, the processor 12 is able to obtain a value of sensitivity as TP/(TP+FN)=80.67%, a value of specificity as TN/(FP+TN)=74.83%, a value of accuracy as (TN+TP)/(TN+FP+FN+TP)=75.23%, a PPV as TP/(TP+FP)=19.03%, a Fi score as (2×sensitivity×PPV)/(sensitivity+PPV)=0.31, an AUC for an ROC curve which is shown in FIG. 6 as 0.864, and an AUC for a PR curve which is shown in FIG. 7 as 0.308. For the ROC curve shown in FIG. 6, the cut-off point (the black dot) corresponds to sensitivity of around 80% and a range of specificity between 70% and 75% (i.e., 25% 1-Specificity 30%). For the PR curve shown in FIG. 7, the cut-off point (the black dot) corresponds to recall (i.e., sensitivity) of around 80% and precision (i.e., PPV) of around 20%.

In summary, the system according to the disclosure establishes a model for cardiac VH screening by using machine learning techniques based on data corresponding to multiple subjects and containing basic physiological parameters, electrocardiographic parameters, and predetermined actual conditions of having or not having cardiac VH relating to the subjects. Because in establishing the model for cardiac VH screening, basic physiological parameters are taken into consideration aside from electrocardiographic parameters, the model for cardiac VH screening established by the system according to the disclosure has an enhanced sensitivity.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A system capable of establishing a model for cardiac ventricular hypertrophy (VH) screening, said system comprising:
    a storage configured to store plural pieces of subject data that are respectively associated with a plurality of subjects, each of the pieces of subject data containing a basic physiological parameter group, an electrocardiographic parameter group, and an actual cardiac VH condition that corresponds to a specified ventricle of one of the subjects associated with the piece of subject data, the specified ventricle being one of a left ventricle and a right ventricle; and
    a processor electrically connected to said storage, and configured to split the pieces of subject data into a training set and a test set, and to establish the model for cardiac VH screening with respect to the specified ventricle based on the pieces of subject data in the training set by using machine learning techniques.

2. The system as claimed in claim 1, wherein the basic physiological parameter group contains values respectively related to an age, a body height and a body weight of the associated one of the subjects.

3. The system as claimed in claim 1, wherein the electrocardiographic parameter group contains values respectively related to a heart rate, a P wave duration in lead II (II-P), a duration of PR segment in lead II (II-PR), a duration of QRS complex in lead II (II-QRS), a duration of QT interval in lead II (II-QT), a duration of corrected QT interval in lead II (II-QTc), a P wave axis in lead II (II-P axis), a QRS axis in lead II (II-QRS axis), a T-wave axis in lead II (II-T axis), an amplitude of R wave in lead I (I-R), an amplitude of R wave in lead II (II-R), an amplitude of R wave in lead III (III-R), an amplitude of R wave in lead augmented vector right (aVR-R), an amplitude of R-wave in lead augmented vector left (aVL-R), an amplitude of S wave in lead augmented vector left (aVL-S), an amplitude of R wave in lead augmented vector foot (aVF-R), an amplitude of R wave in precordial lead V1 (V1-R), an amplitude of S wave in precordial lead V1 (V1-S), an amplitude of R wave in precordial lead V2 (V2-R), an amplitude of S wave in precordial lead V2 (V2-S), an amplitude of R wave in precordial lead V3 (V3-R), an amplitude of S wave in precordial lead V3 (V3-S), an amplitude of R wave in precordial lead V4 (V4-R), an amplitude of S wave in precordial lead V4 (V4 -S), an amplitude of R wave in precordial lead V5 (V5-R), an amplitude of S wave in precordial lead V5 (V5-S), an amplitude of R wave in precordial lead V6 (V6-R) and an amplitude of S wave in precordial lead V6 (V6-S) recorded in an electrocardiogram of the associated one of the subjects.

4. The system as claimed in claim 1, wherein said processor is further configured to:
    perform linear transformation on the pieces of subject data by using min-max normalization so as to generate plural pieces of normalized subject data, where the values contained in the basic physiological parameter group and the electrocardiographic parameter group are mapped into a numeric range [0,1] in the normalized subject data; and
    split the pieces of normalized subject data into the training set and the test set.

5. The system as claimed in claim 1, wherein said processor is configured to establish, by using a support vector machine (SVM) algorithm, the model for cardiac VH screening based on the pieces of subject data in the training set and a target hyperparameter used in the SVM algorithm.

6. The system as claimed in claim 5, wherein said processor is configured to:
    perform data synthesis on the pieces of subject data in the training set to generate plural pieces of synthesized subject data; and
    establish the model for cardiac VH screening based on the pieces of synthesized subject data and the target hyperparameter by using the SVM algorithm.

7. The system as claimed in claim 6, wherein said processor is configured to perform data synthesis on the pieces of subject data in the training set by using synthetic minority over-sampling technique (SMOTE) so as to generate synthetic minority class samples, which form a part of the pieces of synthesized subject data, where the pieces of synthesized subject data belonging to a minority class and the pieces of synthesized subject data belonging to a majority class are substantially equal in number.

8. The system as claimed in claim 5, wherein the training set includes N training subsets, where N is an integer greater than one; and wherein said processor is configured to:
    select one of the N training subsets as a validation subset, and obtain N-1 other subsets which are all the N training subsets except the validation subset;
    perform data synthesis on the pieces of subject data in the N-1 other subsets to generate plural pieces of synthetic subject data; and
    establish, by using the SVM algorithm based on the pieces of synthetic subject data and a plurality of candidate hyperparameters used in the SVM algorithm, a plurality of training models respectively corresponding to the candidate hyperparameters.

9. The system as claimed in claim 8, wherein said processor is configured to perform data synthesis on the pieces of subject data in the N-1 other subsets by using synthetic minority over-sampling technique (SMOTE) so as to generate synthetic minority class samples, which form a part of the pieces of synthetic subject data, where the pieces of synthetic subject data belonging to a minority class and the pieces of synthetic subject data belonging to a majority class are substantially equal in number.

10. The system as claimed in claim 5, wherein the training set includes N training subsets, where N is an integer greater than one, said processor being configured to:
    select one of the N training subsets as a validation subset, and obtain N-1 other subsets which are all the N training subsets except the validation subset;

establish, by using the SVM algorithm based on the pieces of subject data in the N-1 other subsets and a plurality of candidate hyperparameters used in the SVM algorithm, a plurality of training models respectively corresponding to the candidate hyperparameters;
obtain, based on the training models and the pieces of subject data in the validation subset, a plurality of precision-recall (PR) curves respectively corresponding to the candidate hyperparameters;
calculate areas under curves (AUCs) respectively corresponding to the PR curves; and
determine, based on the AUCs, one of the candidate hyperparameters to serve as the target hyperparameter.

11. The system as claimed in claim 5, wherein:
the training set includes N training subsets, where N is an integer greater than one;
said processor is configured to, for each of candidate hyperparameters that are used in the SVM algorithm,
    perform an area under curve (AUC) calculation procedure N number of times so as to obtain N number of AUCs of precision-recall (PR) curves corresponding to the candidate hyperparameter, where the N number of times of performing the AUC calculation procedure respectively corresponding to the N training subsets, and
    calculate an average AUC value based on the N number of AUCs obtained through the N number of times of performing the AUC calculation procedure;
said processor is further configured to determine, based on the average AUC values calculated respectively for the candidate hyperparameters, one of the candidate hyperparameters to serve as the target hyperparameter; and
wherein said processor is further configured to, in each performance of the AUC calculation procedure for each of the candidate hyperparameters,
    select the corresponding one of the N training subsets as a validation subset, and obtain N-1 other subsets which are all the N training subsets except the validation subset,
    establish, by using the SVM algorithm based on the candidate hyperparameter and the pieces of subject data in the N-1 other subsets, a training model corresponding to the candidate hyperparameter,
    obtain, based on the training model and the pieces of subject data in the validation subset, the PR curve corresponding to the candidate hyperparameter, and
    calculate the AUC for the PR curve corresponding to the candidate hyperparameter.

* * * * *